United States Patent [19]
Grubbs et al.

[11] Patent Number: 6,048,993
[45] Date of Patent: Apr. 11, 2000

[54] SYNTHESIS OF RUTHENIUM OR OSMIUM METATHESIS CATALYSTS

[75] Inventors: Robert H. Grubbs, South Pasadena, Calif.; Tomas R. Belderrain, Sevilla, Spain; Seth N. Brown, South Bend, Ind.; Thomas E. Wilhelm, Pasadena, Calif.

[73] Assignee: California Institute of Technology, Pasdena, Calif.

[21] Appl. No.: 09/253,042

[22] Filed: Feb. 19, 1999

Related U.S. Application Data

[62] Division of application No. 08/966,011, Nov. 7, 1997, Pat. No. 5,917,071.
[60] Provisional application No. 60/031,088, Nov. 15, 1996.
[51] Int. Cl.[7] .............................. C07F 9/02; C07F 15/00
[52] U.S. Cl. .............................. 556/21; 556/23; 556/136; 502/162
[58] Field of Search .............................. 556/21, 23, 136, 556/162

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/338 |
| 4,945,141 | 7/1990 | Grubbs et al. | 526/268 |
| 4,945,144 | 7/1990 | Grubbs et al. | 526/268 |
| 5,198,511 | 3/1993 | Brown-Wensley et al. | 526/113 |
| 5,296,566 | 3/1994 | Brown-Wensley et al. | 526/171 |
| 5,312,940 | 5/1994 | Grubbs et al. | 526/136 |
| 5,342,909 | 8/1994 | Grubbs et al. | 526/171 |
| 5,599,962 | 2/1997 | Beatty et al. | 556/21 |
| 5,710,298 | 1/1998 | Grubbs et al. | 556/22 |

OTHER PUBLICATIONS

Burrell, et al., "Synthesis and Reactions of Ru(=CH$_2$) Cl (NO)(PPh$_3$)$_2$, a Stable Terminal Methylene Complex and the Crystal Structure of Ru(CH$_2$PPh$_3$)$_2$($\eta^2$-C$_2$F$_4$Cl (NO)) (PPh$_3$)", J Chem. Soc., Dalton Trans., pp. 609–614, (1991).
Ivin, "Olefin Metathesis" Academic Press, pp. vii–x, 34–36, (1983).
McGrath, et al., "Aqueous Ring–Opening Metathesis Polymerization of 7–Oxanorbornene Derivatives Using Ruthenium Catalysts", Olefin Metathesis and Polymerization Catalysts, pp. 526–536, (1990).
Novak, et al., "Catalytic Organometallic Chemistry in Water: The Aqueous Ring–Opening Metathesis Polymerization of 7–Oxanorbornene Derivatives", J. Am. Chem. Soc. 110, pp. 7542–7543, (1988).
Hillmyer, et al., "The Aqueous Ring–Opening Metathesis Polymerization of exo–N–Methyl–7–oxabicyclo [2.2.1] hept–5–ene–2, 3–dicarbonximide" pp. 162–163 (1991).
Carter, et al., "Review of the Chemistry of Cyclopropane Compounds", Chemical Reviews 64 (5), pp. 497–525, (1964).
Schmidbaur, et al., "Ylide Chemistry: An Account of Structural, Conformational and Redox Investigations", Phosphorous and Sulfur 18, pp. 167–170 (1983).

"Metathesis of Functionalized Olefins", J. of Molecules Catalysis 15, pp. 35–45 (1982).
Collman, et al., "Radical Mechanism for the Decomposition of RuOEP(CH$_2$CH$_3$)$_2$. Determination of the Metal–Carbon Bond Dissociation Energy," J Am. Soc. 108, pp. 1332–1333 (1986).
Bruce, et al., "Cyclopentadienyl–Ruthenium and —Osmium Chemistry. Some Reactions of Substituted Vinylidene Complexes," J. Org. Chem. 171: C5–C8 (1979).
Green, et al., "Carbene Complexes of Iron, Molybdenum and Ruthenium: A New Route to Metal–Carbene Derivatives," J. Chem. Soc. (A), pp. 794–797 (1971).
LeBozec, et al., "A New Route to Vinylcarbene Metal Complexes in One Step from 2–Propan–1–ols and Arene Ruthenium(II) Derivatives," J. Chem. Soc., Chem. Comm. pp. 219–221 (1989).
Nguyen, et al. "Ring–Opening Metathesis Polymerization (ROMP) of Norbornene by a Group VIII Carbene Complex in Protic Media," J. Am. Chem. Soc. 114, pp. 3974–3975 (1992).
Grundy, et al., "Migratory–Insertion Reactions of Osmium (II) Ethyl Complexes Derived from an Osmium (0) Ethylene Complex," J. Org. Chem. 216, pp. 255–262, (1981).
Grundy, et al., "Propionyl Complexes of Ruthenium Derived from the Reaction of Ethylene with RuHCl(CO$_2$)(PPh$_3$)$_2$," J. Org. Chem., 265, pp. 77–85 (1984).

(List continued on next page.)

Primary Examiner—Porfirio Nazario-Gonzalez
Attorney, Agent, or Firm—Pillsbury Madison & Sutro LLP

[57] ABSTRACT

The present invention relates to the synthesis of highly active ruthenium and osmium carbene metathesis catalyst in good yield from readily available starting materials. The catalysts that may be synthesized are of the general formula

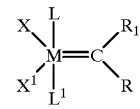

wherein:
  M is ruthenium or osmium;
  X and X$^1$ are independently any anionic ligand;
  L and L$^1$ are any neutral electron donor ligand; and,
  R and R$^1$ are each hydrogen or one of the following substituent groups: C$_2$–C$_{20}$ alkenyl, C$_2$–C$_{20}$ alkynyl, C$_1$–C$_{20}$ alkyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl and C$_1$–C$_{20}$ alkylsulfinyl. Specific synthetic protocols for vinyl alkylidene catalysts wherein R is hydrogen and R$^1$ is —CHCR$^{12}$R$^{13}$ and non-vinyl alkylidene catalysts are also disclosed. In addition to the ease of synthesis (typically a one-step synthesis), the reactions generally may be run at or above room temperature and the resulting products usually may be used without extensive post synthesis purification.

34 Claims, No Drawings

OTHER PUBLICATIONS

Schrock, et al., "Living Ring–Opening Metathesis Polymerization Catalyzed by Well Characterized Transition Metal Alkylidene Complexes," Acc. Chem. Res. 23, pp. 158–165, (1990).

Fu, et al., "Catalytic Ring–Closing Metathesis of Functionalized Dienes by a Ruthenium Carbene Complex", J. Am. Chem. Soc., 115, pp. 9856–9857, (1993).

Grubbs, et al., "Ring–Opening Metathesis Polymerization Catalysts", Polymer Preprints, 35(1), p. 688 (1994).

Hillmyer, et al. "The ROMP of COD By a Well–defined Metathesis Catalyst in the Presence of a Difunctional Chain Transfer Agent: The Preparation of Hydroxy–telechelic 1,4–Poly(butadiene)," Polymer Preprints, 34(2), pp. 388.

Hillmyer, et al. "Preparation of Hydroxytelechelic Poly(butadiene) via Ring–Opening Metathesis Polymerization Employing a Well–defined Metathesis Catalyst", Macromolecules 26 (4), pp. 872–874 (1992).

Nguyen, et al., "Syntheses and Activities of New Single–Component Ruthenium–Based Olefin Metathesis Catalysts", J. Am. Chem. Soc. 115 (21), pp. 9858–9859 (1993).

Schwab, et al., "A series of Well–Defined Metathesis Catalysts– Synthesis of [RuCl$_2$(=CHR$'$) (PR$_3$)$_2$] and its Reactions", Angew. Chem. Int. Ed. Engl., 34 (18), pp. 2039–2411, (1995).

Schwab, et al., "Synthesis and Applications of RuCl$_2$ (=CHR$'$) (PR$_3$)$_2$: The Influence of the Alkylidene Moiety on Metathesis Activity", J. Am. Chem. Soc., 118 (1), pp. 100–110, (1996).

Chaudret, et al., "The Use of (Cyclo–octadiene)(Cyclo–octatriene) Ruthenium (0) as the Starting Material for the Synthesis of Mono– and Poly–nuclear Ruthenium Polyhydride Phosphine Complexes," J. Chem. Soc., Chem. Comm., pp. 1388–1390, (1992).

"($\eta^6$–Cycloocta–1,3,5–triene)($\eta^4$–cycloocta–1,5–diene) Ruthenium (0) in the Development of Ruthenium Chemistry", Comments Inorg. Chem. 11 (4), pp. 175–194, (1991).

Komiya, et al., "Reactions of Dihydridotetrakis(triphenylphosphine)ruthenium(II) with Olefins and Isolation of New Ruthenium–Olefin Complexes", Bulletin of the Chem. Soc. Of Japan 49 (9), pp. 2553–2559, (1976).

Cenini, et al., "Low Oxidation States Ruthenium Chemistry. I. The Reaction of Ru(PPh$_3$)$_3$ Cl$_2$ and Related Complexes with Small Molecules", Gazzetta Chimica Italiana 105, pp. 255–273, (1975.

Frosin, et al., "The Reduction of Hydrated Ruthenium (III) Chloride with Zinc in the Presence of Cyclooctadiene: Molecular Structure of Ru(C$_8$H$_{10}$)(C$_8$H$_{12}$) and Isolation and X–ray Structural Characterization of Ru$_2$Cl$_4$(C$_8$H$_{12}$)$_2$, RuH(C$_8$H$_{11}$)(C$_6$H$_6$) and Ru$_3$Cl$_3$(OCH$_3$)(C$_8$H$_{12}$)$_3$", Inorg. Chimica Acta 167, pp. 83–89, (1990).

Deeming, et al., "Reactivity of Coordinated Ligands. Part XX. Preparation and Reactions of Cyclooctadiene Comleses of Iron, Ruthenium and Osmium," J. Chem. Soc. Dalton, pp. 2093–2104 (1974).

Komiya, et al., "C–O Bond Cleavage and Oxidative Addition of Allyl Carboxylate to Ruthenium (0) Complex. Isolation of ($\pi$–allyl)(tri–fluoroace–tato)tris(triethylphosphine)ruthenium(II)", J. Org. Chem., 471, pp. C6–C7 (1994).

Sabo–Etienne, et al., "Substitution Reactions of Coordinated Dihydrogen by Weakly Coordinating Ligands. Preparation of RuH$_2$(N$_2$)$_2$(PCy$_3$)$_2$ and RuH$_2$($\eta^2$–H$_2$)(HEPh$_3$)(PCy$_3$)$_2$ (E= Si, Ge)," New J. Chem. 18, pp. 175–177, (1994).

Esteruelas, et al., "Reactions of RuHCl(CO)(PiPr$_3$)$_2$ with Alkyn–1–ols: Synthesis of Ruthenium (II) Hydroxyvinyl and Vinylcarbene Complexes", Organometallics 13, pp. 4258–4265, (1994).

Esteruelas, et al., "Reactions of the Dihydrogen Complex OsCl$_2$($\eta^2$–H$_2$)(CO)(PiPr$_3$)$_2$ with Terminal Alkynes: Synthesis of Carbene, Vinylcarbene and $\mu$ –Bis–carbene Osmium(II) Derivatives" J. Am. Chem. Soc. 117 (30), pp. 7935–7942, (1995).

Esteruelas, et al., "Five Coordinate Complex [RuHCl(CO)(PPr$^{i_3}$)$_2$] as a Precursor for the Preparation of New Cyclopentadienylruthenium Compounds Containing Unsaturated $\mu^1$–Carbon Ligands", Organometallics 15.

Komiya, et al., "Reactions of Hydrido Complexes of Ruthenium and Rhodium with Carbon Dioxide Involving Reversible Insertion", J. Org. Chem 46, pp. C58–c60, (1972).

Chaudret, et al., "Preparation of Polyhydride Complexes of Ruthenium by Direct Hydrogenation of Zerovalent Olefinic Derivatives. Mononuclear Complexes of the Type RuH$_6$L$_2$ and RuH$_4$L$_3$. Spontaneous H–D Exchange Between the Phosphine Protons and the Solvent Catalyzed by RuH$_4$L$_3$", Organometallics 4 (10), pp. 1722–1726, (1985).

Christ, et al., "Highly Selective Dehydrogenative Silylation of Ethylene Using the Bis(dihydrogen) Complex RuH$_2$(H$_2$)$_2$(PCy$_3$)$_2$ as Catalyst Precursor", Organometallics 14 (3), pp. 1082–1084 (1995).

Christ, et al., "Synthesis, Characterization and Chemistry of 16–electron Dihydrogen Complexes of Ruthenium", Organometallics 13 (10), pp. 3800–3804 (1994).

Grunwald, et al., "Five Coordinate 16–electron Carbene and Vinylidenruthenium (II) Complexes Prepared from [RuCl$_2$(C$_8$H$_{12}$)]$_n$ or from the New Dihydridoruthenium (IV) Compound [RuH$_2$Cl$_2$(P$^i$Pr$_3$)$_2$]", Organometallics 15 (8), pp. 1960–1962, (1996).

SYNTHESIS OF RUTHENIUM OR OSMIUM METATHESIS CATALYSTS

The present application is a divisional of Ser. No. 08/966,011 filed Nov. 7, 1997, now U.S. Pat. No. 5,917,071, entitled SYNTHESIS OF RUTHENIUM OR OSMIUM METATHESIS CATALYSTS by inventors Robert H. Grubbs, Tomas R. Belderrain, Seth N. Brown, and Thomas E. Wilhelm which is incorporated herein by reference, which claims the benefit of U.S. Provisional Application No. 60/031,088, filed Nov. 15, 1996 by inventors Robert H. Grubbs, Tomas Belderrain, and Seth N. Brown entitled "Synthesis of Ruthenium Metathesis Catalysts from Ruthenium Hydride Complexes" which is also incorporated herein by reference.

The U.S. Government has certain rights in this invention pursuant to Grant No. CHE 9509745 awarded by the National Science Foundation.

BACKGROUND

The present invention relates to the synthesis of highly active ruthenium or osmium carbene metathesis catalysts. To the synthetic organic or polymer chemist, simple methods for forming carbon-carbon bonds are extremely important and valuable tools. One method of C—C bond formation that has proved particularly useful is transition-metal catalyzed olefin metathesis. The past two decades of intensive research effort has recently culminated in the discovery of well defined ruthenium and osmium carbene complex catalysts that are highly metathesis active and stable in the presence of a variety of functional groups.

These ruthenium and osmium carbene complexes have been described in U.S. Pat. Nos. 5,312,940 and 5,342,909 and U.S. patent applications Ser. Nos. 08/708,057, 08/282,827 and 08/693,789, all of which are incorporated herein by reference. The ruthenium and osmium carbene complexes disclosed in these patents and applications all possess metal centers that are formally in the +2 oxidation state, have an electron count of 16, and are penta-coordinated. These catalysts are of the general formula

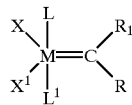

where M is ruthenium or osmium, X and $X^1$ are anionic ligands, and L and $L^1$ are neutral electron donors and R and R' are specific substituents that will be described in more detail below.

U.S. Pat. Nos. 5,312,940 and 5,342,909 disclose specific vinyl alkylidene ruthenium and osmium complexes in which the neutral electron donor ligands L and $L^1$ are triphenyl phosphines or diphenylmethyl phosphines. As disclosed in the patents, the catalysts are useful in catalyzing the ring opening metathesis polymerization ("ROMP") of strained olefins. U.S. patent applications Ser. Nos. 08/708,057 and 08/282,827 disclose specific vinyl alkylidene ruthenium and osmium complexes in which the neutral electron donor ligands L and $L^1$ are phosphines with at least one secondary-alkyl or cycloalkyl substituent. These secondary-alkyl phosphine catalysts are more metathesis active than the corresponding triphenyl phosphine catalysts and may be used to catalyze a variety of metathesis reactions involving acyclic and unstrained cyclic olefins. U.S. patent application Ser. No. 08/693,789 discloses specific non-vinyl alkylidene complexes that are more metathesis active than their vinyl alkylidene counterparts. The preferred catalyst disclosed in this application are benzylidene ruthenium and osmium carbene compounds.

As disclosed by U.S. Pat. Nos. 5,312,940 and 5,342,909, vinyl alkylidene catalysts may be synthesized by a variety of methods including the reaction of ruthenium or osmium compounds with cyclopropenes or phosphoranes, and neutral or anionic ligand exchange. Of these previous methods, the preferred method of making the catalysts is via the reaction of a substituted cyclopropene with a ruthenium or osmium dihalide. Unfortunately, this method is limited to the synthesis of vinyl alkylidene catalysts (i.e., catalysts in which R is hydrogen and $R^1$ is a substituted vinyl group) and cannot be used to directly synthesize the secondary-alkyl phosphine catalysts disclosed in the Ser. Nos. 08/282,826 and 08/282,827 applications. The synthesis of these secondary-alkyl phosphine catalysts further requires reacting the triphenyl phosphine catalysts produced from the cyclopropene reaction with secondary-alkyl phosphines in a ligand exchange reaction.

In part to overcome the fact that the cyclopropenes are not readily available and are generally limited to the synthesis of vinyl alkylidene catalysts, U.S. patent application Ser. No. 08/693,789 discloses a method for synthesizing alkylidene complex catalysts via the reaction of substituted diazoalkanes with ruthenium dihalides. The synthetic procedures disclosed in this application can be used to make non-vinyl alkylidene complex catalysts which are more metathesis active than their corresponding vinyl alkylidene counterparts. As in the cyclopropene based methods, the secondary-alkyl phosphine catalysts cannot be synthesized directly from the reaction of ruthenium dihalide and diazoalkanes. Instead, the secondary-alkyl phosphine catalysts must be synthesized by ligand exchange. Although the use of diazo starting materials greatly broadened the range of ruthenium and osmium carbene catalysts that could be synthesized, the danger of handling diazocompounds on a large scale severely restricts the commercial and laboratory utility of this method. In addition, the diazo method requires the synthesis to be conducted at low temperature (about −80° C. to −50° C.) and requires the use of considerable solvent in the final purification of the catalyst. As with the cyclopropene synthesis method, the secondary-alkyl phosphine catalysts must be synthesized using a multi-step ligand exchange procedure which may be time consuming and expensive and may result in lower product yields.

In both the cyclopropene and diazo synthesis methods the secondary-alkyl phosphine catalysts must be synthesized using a multi-step, ligand exchange procedure. Since the secondary-alkyl phosphine catalysts are more metathesis active than the triphenyl phosphine catalysts and therefore may have wider commercial utility, the necessity of a multi-step synthesis in these cases can be a severe limitation.

Although the previous methods have been adequate to make reasonable quantities of the ruthenium and osmium carbene catalysts, as the number of scientific and commercial applications of these catalysts continues to increase, a need exists for simple, safe, and inexpensive methods of synthesizing these compounds to fully exploit their potential.

SUMMARY

The present invention addresses this need and provides simple, safe, and less expensive methods of synthesizing ruthenium and osmium carbene catalysts. In general, one step syntheses are provided using stable, readily available starting materials. The processes result in good product yield without the need for expensive and sophisticated equipment. In addition, both vinyl and non-vinyl alkylidene catalysts may be synthesized. Moreover, the methods can produce catalysts in a form which makes post synthesis purification unnecessary.

In one aspect of the present invention, a method for synthesizing ruthenium and osmium carbene complex catalysts of the formula

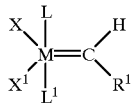

is provided where M is ruthenium or osmium; X and $X^1$ are any anionic ligand, preferably chloride; and L and $L^1$ are any neutral electron donor ligand, preferably tricycloalkylphosphines; and, $R^1$ may be any one of a variety of substituents which are described in detail below. In the preferred catalyst, $R^1$ is phenyl. In this embodiment of the invention, a compound of the formula

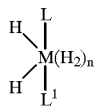

(n=1 or 2) is contacted with a compound of the formula $R^1C(X)(X^1)H$ in the presence of an olefin to yield the required ruthenium or osmium carbene complex catalyst.

In another aspect of the present invention, a method for synthesizing vinyl alkylidene catalysts of the formula

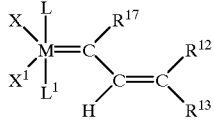

is provided where M, X, $X^1$, L, and $L^1$ are as described above and $R^{12}$, $R^{13}$, and $R^{17}$ may be the same or different and may be any one of a variety of substituents that are described in detail below. In the preferred catalyst, $R^{12}$ and $R^{13}$ are the same and are both methyls and $R^{17}$ is hydrogen. In this embodiment of the invention, a compound of the formula

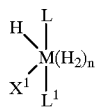

(n=1 or 2) is contacted with a compound of the formula

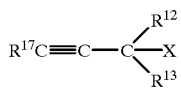

to yield the required ruthenium or osmium carbene complex catalyst.

Alternatively, the alkyne may be of the general formula, $R^{17}C\equiv CCR^{12}R^{13}R'$, wherein R' is hydroxyl. In this variation, the alkyne is reacted with the dihydrogen complex as above but then subsequently reacted with HX to form the above described vinyl alkylidene catalyst. However, in another variation of this reaction scheme, when R' is hydrogen or a $C_1$–$C_{20}$ alkyl, the method produces a non-vinyl alkylidene catalyst of the general formula, $(X)(X^1)(L)(L^1)M=C(R^{17})(CH_2CR^{12}R^{13}R')$ In yet another aspect of the present invention, a method for synthesizing compounds of the formula

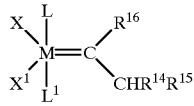

is provided where M, X, $X^1$, L, and $L^1$ are as described above and $R^{14}$, $R^{15}$ and $R^{16}$ may be any one of a variety of substituents that are described in detail below. In this embodiment of the invention, a compound of the formula

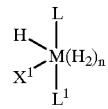

(n=1 or 2) is contacted with a compound of the formula

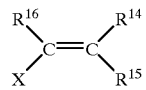

to yield the required ruthenium or osmium carbene complex catalyst.

DETAILED DESCRIPTION

General Description of the Catalysts

The methods of the present invention may be used to synthesize ruthenium or osmium carbene complex catalysts that include a ruthenium or osmium metal center that is in a +2 oxidation state, have an electron count of 16, and are penta-coordinated. More specifically, the methods of the present invention may be used to synthesize compounds with the formula

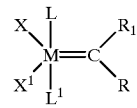

wherein:
M is ruthenium or osmium;
X and $X^1$ are independently any anionic ligand;
L and $L^1$ are any neutral electron donor ligand;
R and $R^1$ are each hydrogen or one of the following substituent groups: $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the $R^1$ substituent may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In a preferred embodiment, the R substitutent is hydrogen and the $R^1$ substituent is one of the following: (1) hydrogen; (2) $C_1$–$C_{20}$ alkyl; (3) $C_2$–$C_{20}$ alkenyl (4) aryl; (5) $C_1$–$C_{20}$ alkyl substituted with one or more groups selected from the group consisting of aryl, halogen, hydroxy, $C_1$–$C_5$ alkoxy, and $C_2$–$C_5$ alkoxycarbonyl; and (6) aryl substituted with one or more groups selected from the group consisting of $C_1$–$C_5$ alkyl, aryl, hydroxyl, $C_1$–$C_5$ alkoxy, amino, nitro, and halogen. In a more preferred embodiment, the $R^1$ substituent is phenyl or phenyl substituted with a group selected from the group consisting of chloride, bromide, iodide, fluoride, —$NO_2$, —$NMe_2$, methoxy, and methyl. In the most preferred embodiment, the $R^1$ substituent is phenyl.

The L and $L^1$ ligands may be the same or different and may be any neutral electron donor ligand. In a preferred embodiment, the L and $L^1$ ligands may be the same or different and may be phosphines, sulfonated phosphines, phosphites, phosphinites, phosphonites, arsines, stibines, ethers, amines, amides, imines, sulfoxides, carboxyls, nitrosyls, pyridines, and thioethers. In a more preferred embodiment, the L and $L^1$ ligands may be the same or different and are phosphines of the formula $PR^3R^4R^5$, where $R^3$ is a secondary alkyl or cycloalkyl group, and $R^4$ and $R^5$ are the same or different and may be aryl, $C_1$—$C_{10}$ primary alkyl, secondary alkyl, or cycloalkyl groups. In the most preferred embodiment, the L and $L^1$ ligands may be the same or different and are —P(cyclohexyl)$_3$, —P(cyclopentyl)$_3$, or —P(isopropyl)$_3$.

The X and $X^1$ ligands may be the same or different and may be any anionic ligand. In a preferred embodiment, the X and $X^1$ ligands may be the same or different and may be a halogen, hydrogen or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Each group may optionally be substituted with $C_1$–$C_5$ alkyl, halogen, $C_1$–$C_5$ alkoxy or with a phenyl group. The phenyl group in turn may optionally be substituted with halogen, $C_1$–$C_5$ alkyl or $C_1$–$C_5$ alkoxy. In a more preferred embodiment, the X and $X^1$ ligands may be the same or different and may be chloride, bromide, iodide, hydrogen or a moiety selected from a group consisting of: benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. Each moiety may optionally be substituted with $C_1$–$C_5$ alkyl or a phenyl group. The phenyl group may optionally be substituted with halogen, $C_1$–$C_5$ alkyl or $C_1$–$C_5$ alkoxy. In an even more preferred embodiment, the X and $X^1$ ligands may be the same or different and may be chloride, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiment, X and $X^1$ are both chloride.

The most preferred catalysts are

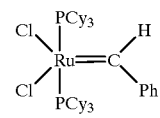

and

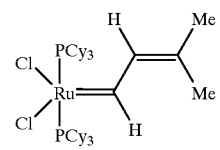

where Cy is cyclohexyl or cyclopentyl and Me is methyl.

The above catalysts are stable in the presence of a variety of functional groups including hydroxyl, thiol, ketone, aldehyde, ester, ether, amine, imine, amide, nitro, carboxylic acid, disulfide, carbonate, isocyanate, carbodiimide, carboalkoxy, and halogen. Therefore, the starting materials and products of the reactions described below may contain one or more of these functional groups without poisoning the catalyst. In addition, the catalysts are stable in the presence of aqueous, organic, or protic solvents, for example, aromatic hydrocarbons, chlorinated hydrocarbons, ethers, aliphatic hydrocarbons, alcohols, water, or mixtures of the above. Therefore, the reactions described below may be carried out in one or more of these solvents without poisoning the catalyst product.

General Synthetic Schemes

The present invention relates to new routes for synthesizing the above-described ruthenium and osmium carbene catalysts which eliminate many of the problems associated with previous methods. Unless explicitly stated otherwise, the substituents of the catalyst are as defined above.

We have discovered that the ruthenium and osmium carbene catalysts may be synthesized in one-step syntheses using readily available and stable carbene and metal sources. As will be described in detail below, the methods of the present invention allow for the synthesis of ruthenium and osmium carbene complex compounds without the use of unstable starting materials and using reactions that may be run at room temperature or above. The method also allows for the preparation of catalysts with varying anionic and neutral electron donor ligands and varying substituents on the carbene carbon. The methods of the present invention generally yield the carbene complexes in greater than 90% yield and are sufficiently clean that the resulting catalysts may be used without extensive post synthesis purification. As discussed in the background section, all of these aspects of the present invention possess important advantages over the existing methods.

We have discovered three routes through which the catalysts may be synthesized involving a ruthenium or osmium dihydrogen complex and a simple organic compound. The two general forms of the dihydrogen complex are $M(H)_2(H_2)_nL^1L$ and $M(H)X(H_2)_nL^1L$ wherein M, X, L and $L^1$ are as previously defined and n is 1 or 2. Because the dissociation of the first dihydrogen species is facile, the single dihydrogen (n=1) and bis(dihydrogen) (n=2) complexes are essentially interchangeable. In general, the bis(dihydrogen) complex predominates in the solid form of the complex and the single(dihydrogen) complex predominates in solution.

In the first route, the dihydrogen complex is $M(H)_2(H_2)_nL^1L$ and the organic compound is a substituted alkane which includes a carbon atom bearing the $X$, $X^1$, and $R^1$ substituents of the catalyst. In the second route, the dihydrogen complex is $M(H)(X)(H_2)_nL^1L$ and the organic compound is a substituted alkyne. In the third route, the dihydrogen complex is $M(H)(X)(H_2)_nL^1L$ and the organic compound is an alkene (olefin).

For clarity and ease of presentation, specific reaction conditions and procedures are collected together in the final Experimental Procedures section.

The Alkane Route

This embodiment of the invention may be summarized in Reaction Scheme 1, below.

REACTION SCHEME 1

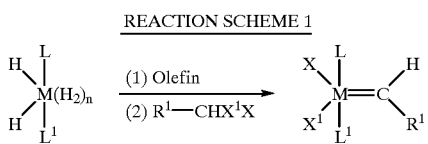

This embodiment includes a process for synthesizing a compound of the formula

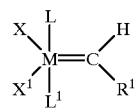

which comprises the step of contacting a compound of the formula

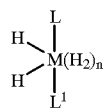

with a compound of the formula $R^1C(X)(X^1)H$ in the presence of an olefin. M, $R^1$, X, $X^1$, L, and $L^1$ are as described defined in the catalysts section and n is either 1 or 2.

In preferred embodiments of the alkane method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C_1-C_{10}$ primary alkyl, secondary alkyl, or cycloalkyl groups; X and $X^1$ ligands are each a halogen, benzoate, $C_1-C_5$ carboxylate, $C_1-C_5$ alkyl, $C_1-C_5$ alkoxy, $C_1-C_5$ alkylthio, aryl, or $C_1-C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2CO$, Pho, MeO, EtO, tosylate, mesylate, and trifluoromethanesulfonate; $R^1$ is hydrogen or a substituted or unsubstituted $C_1-C_{20}$ alkyl or aryl wherein the substituted group is selected from a group consisting of aryl, halogen, hydroxy, amino, nitro, $C_1-C_5$ alkyl, $C_1-C_5$ alkoxy, and $C_2-C_5$ alkoxycarbonyl; and the olefin is one which does not readily undergo metathesis reactions or regenerate the same species upon metathesis.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^1$ substituent is an substituted or an unsubstituted aromatic hydrocarbon wherein the substituted group is selected from the group consisting of chloride, bromide, iodide, fluoride, —NO$_2$, —NMe$_2$, methoxy, and methyl; and the olefin is cyclohexene or styrene.

In the most preferred embodiments: L and $L^1$ ligands are each either —P(cyclohexyl)$_3$ or —P(cyclopentyl)$_3$; X and $X^1$ ligands are each chloride; $R^1$ substituent is a substituted or unsubstituted phenyl wherein the substituted group is selected from the group consisting of chloride, bromide, iodide, fluoride, —NO$_2$, —NMe$_2$, methoxy, and methyl; and the olefin is cyclohexene.

As stated previously, it is preferred that the olefin selected for use in this synthetic route is one which does not readily undergo metathesis. When a metathesis active olefin such as ethylene is used, the expected product may not be generated in high yields due to a potential metathesis reaction between the olefin and the product catalyst. For example, when $Ru(H)_2(H_2)_2(PCy_3)_2$ was reacted with either $PhCHCl_2$ or $Cl_2CHCO_2Me$ in the presence of ethylene, instead of the expected benzylidene and ester carbene, a methylidene complex was formed. Observations of the carbene proton resonances of the intermediates ($\delta$=20.59 and 20.15 respectively) as well as the formation of styrene and methyl methacrylate confirm that this is due to the subsequent metathesis reaction of ethylene with the resulting benzylidene and ester carbene.

However, this subsequent metathesis reaction is substantially eliminated when a less active olefin is used such as cyclohexene. For example, when $Ru(H)_2(H_2)_2(PCy_3)_2$ was reacted with $PhCHCl_2$, $Cl_2CHCO_2Me$ or $CH_2Cl_2$ in the presence of cyclohexene, the corresponding carbenes were formed in good yield. When these reactions were monitored by $^{31}P$ NMR using triphenylphosphine oxide as the internal standard, the NMR experiments showed that these conversions were essentially quantitative.

Alkyne Route

One version of this embodiment of the invention may be summarized in Reaction Scheme 2, below.

REACTION SCHEME 2

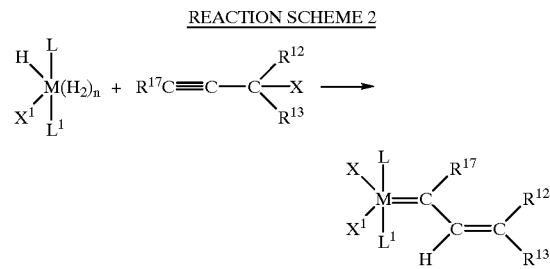

This embodiment includes a process for synthesizing a compound of the formula

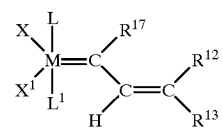

which comprises the step of contacting a compound of the formula

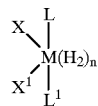

with a compound of the formula

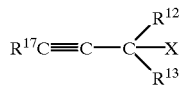

wherein M, X, $X^1$, L, and $L^1$ are as previously defined in the catalysts section.

Alternatively, the alkyne may be of the general formula, $R^{17}C{\equiv}CCR^{12}R^{13}R'$, wherein R' is hydroxyl. In this variation, the alkyne is reacted with the dihydrogen complex as above but then subsequently reacted with HX to form the above described catalyst. However, in another variation of this reaction scheme, when R' is hydrogen or a $C_1$–$C_{20}$ alkyl, the method produces a catalyst of the general formula, $(X)(X^1)(L)(L^1)M{=}C(R^{17})(CH_2CR^{12}R^{13}R')$.

In either version, the remaining variables are n which is either 1 or 2; $R^{17}$ which is hydrogen, aryl or $C_1$–$C_{18}$ alkyl; and $R^{12}$ and $R^{13}$ which are each hydrogen or one of the following substituent groups: $C_1$–$C_{18}$ alkyl, $C_2$–$C_{18}$ alkenyl, $C_2$–$C_{18}$ alkynyl, aryl, $C_1$–$C_{18}$ carboxylate, $C_1$–$C_{18}$ alkoxy, $C_2$–$C_{18}$ alkenyloxy, $C_2$–$C_{18}$ alkynyloxy, aryloxy, $C_2$–$C_{18}$ alkoxycarbonyl, $C_1$–$C_{18}$ alkylthio, $C_1$–$C_{18}$ alkylsulfonyl and $C_1$–$C_{18}$ alkylsulfinyl; wherein the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the $R^{12}$ and $R^{13}$ substituent groups may further include one or more functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of the alkyne method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C_1$–$C_{10}$ primary alkyl, secondary alkyl, or cycloalkyl groups; X and $X^1$ ligands are each a halogen, benzoate, $C_1$–$C_5$ carboxylate, $C_1$–$C_5$ alkyl, $C_1$–$C_5$ alkoxy, $C_1$–$C_5$ alkylthio, aryl, or $C_1$–$C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; $R^{12}$ and $R^{13}$ are each substituted or unsubstituted $C_1$–$C_{18}$ alkyl or aryl wherein the substituted group is selected from a group consisting of aryl, halogen, hydroxy, amino, nitro, $C_1$–$C_5$ alkyl, $C_1$–$C_5$ alkoxy, and $C_2$–$C_5$ alkoxycarbonyl; and $R^{17}$ is hydrogen or methyl.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^{12}$ and $R^{13}$ are each substituted or unsubstituted aromatic hydrocarbon wherein the substituted group is selected from the group consisting of chloride, bromide, iodide, fluoride, —$NO_2$, —$NMe_2$, methoxy, and methyl; and $R^{17}$ is hydrogen.

In the most preferred embodiments: L and $L^1$ ligands are each either —P(cyclohexyl)$_3$ or —P(cyclopentyl)$_3$; X and $X^1$ ligands are each chloride; $R^{12}$ and $R^{13}$ are each substituted or unsubstituted phenyl or wherein the substituted group is selected from the group consisting of chloride, bromide, iodide, fluoride, —$NO_2$, —$NMe_2$, methoxy, and methyl; and $R^{17}$ is hydrogen.

This embodiment of the invention is an extremely efficient method for synthesizing the above described ruthenium and osmium vinyl alkylidene catalysts in essentially a one pot synthesis. Because the metal complex need not be isolated, it may be generated in situ and then subsequently reacted with a substituted alkyne to form the desired product.

In addition to the ease of synthesis, the embodiment also results in high product yields. For example, the hydrido chloride complex $Ru(H)(Cl)(H_2)(PCy_3)_2$ reacts rapidly with commercially available 3-chloro-3-methyl-1-butyne in methylene chloride to form the carbene complex $Ru(Cl)_2(PCy_3)_2({=}CH{-}CH{=}Me_2)$ in 95.2% isolated yield. When this reaction was monitored by $^1$H NMR, it was found that the reaction is completed in less than ten minutes, even at $-30°$ C. At this temperature, integration against an internal standard reveals that the yield is approximately 99.5%.

Reactions with other alkynes, especially propargylic halides, were found to react similarly. Ruthenium carbenes $Ru(Cl_2)(PCy_3)_2({=}CH{-}CH{=}(CH_2)_5)$ and $Ru(Cl_2)(PCy_3)_2$ (${=}CH{-}CH{=}CHPh$) were formed from the corresponding alkynes in essentially quantitative yields, although a trace of the ruthenium (IV) complex, $Ru(H)_2(Cl)_2(PCy_3)_2$ was formed as a byproduct. Interestingly, the amount of the byproduct increased as the steric bulk of the alkyne decreased. For example, the monomethyl substituted $HC{\equiv}CCH(CH_3)Cl$ formed the carbene product $Ru(Cl)_2(PCy_3)_2({=}CH{-}CH{=}Me)$ and the byproduct $Ru(H)_2(Cl)_2(PCy_3)_2$ in an 8:1 ratio, and $HC{\equiv}CCH2Cl$ formed the carbene product $Ru(Cl)_2(PCy_3)_2({=}CH{-}CH{=}CH_2)$ and the byproduct in a 0.8:1 ratio.

Changing X also affected the amount of the byproduct formed. For example, the dimethyl-substituted propargyl bromide, $HC{\equiv}CC(Me)_2Br$ gives 30:1 of the expected mixed halogen carbene $RuClBr(PCy_3)_2({=}CH{-}CH{=}CMe_2)$ to the mixed halogen Ru(IV) species $RuClBr(H)_2(PCy_3)_2$ which is substantially different than from the greater than 200:1 ratio seen with the corresponding chloride, $HC{\equiv}CC(Me)_2Cl$. As a result, tertiary propargylic halide, especially tertiary propargylic chlorides are most preferred.

Moreover, ratio of carbene to Ru(IV) byproduct can be improved dramatically if the solvent is changed from dichloromethane to benzene or toluene. By switching solvents, the 8:1 and 0.8:1 product to byproduct ratios of $HC{\equiv}CCH(CH_3)Cl$ and $HC{=}CCH_2Cl$ were improved to 30:1 and 37:1 respectively.

When L and $L^1$ groups are triaryl phosphines, Reaction Scheme 2 may be modified by replacing a dihydrogen species in the starting complex with a third phosphine ligand. The resulting hydrido complex will be of the form $M(H)(Cl)(H_2)LL^1L^2$ or $M(H)(Cl)LL^1L^2$ depending on the starting dihydrogen species. In all other respects, M, X, $X^1$, $R^{12}$, $R^{13}$, and $R^{17}$ are as described above. Reaction Scheme 2A shows one version of this embodiment.

REACTION SCHEME 2A

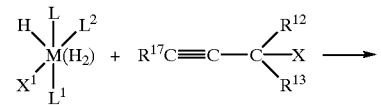

-continued

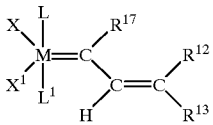

Alkene Route

This embodiment of the invention may be summarized in Reaction Scheme 3, below.

REACTION SCHEME 3

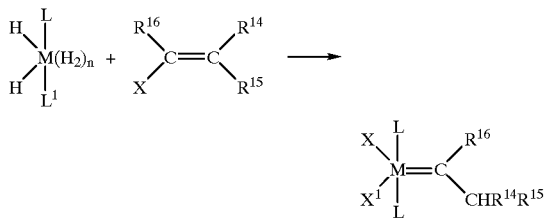

This embodiment includes a process for synthesizing a compound of the formula

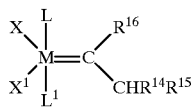

This process comprises the step of contacting a compound of the formula

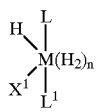

with a compound of the formula

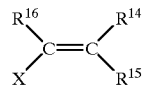

M, X, $X^1$, L, and $L^1$ are as described defined in the catalysts section; n is either 1 or 2; and $R^{14}$, $R^{15}$, and $R^{16}$ are each is hydrogen or one of the following substituent groups: $C_1$–$C_{19}$ alkyl, $C_2$–$C_{19}$ alkenyl, $C_2$–$C_{19}$ alkynyl, aryl, $C_1$–$C_{19}$ carboxylate, $C_1$–$C_{19}$ alkoxy, $C_2$–$C_{19}$ alkenyloxy, $C_2$–$C_{19}$ alkynyloxy, aryloxy, $C_2$–$C_{19}$ alkoxycarbonyl, $C_1$–$C_{19}$ alkylthio, $C_1$–$C_{19}$ alkylsulfonyl and $C_1$–$C_{19}$ alkylsulfinyl; wherein the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the $R^{14}$, $R^{15}$, and $R^{16}$ substituent groups may further include one or more functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of the alkene method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C^1$–$C_{10}$ primary alkyl, secondary alkyl, or cycloalkyl groups; X and $X^1$ ligands are each a halogen, benzoate, $C_1$–$C_5$ carboxylate, $C_1$–$C_5$ alkyl, $C_1$–$C_5$ alkoxy, $C_1$–$C_5$ alkylthio, aryl, or $C_1$–$C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; $R^{14}$ and $R^{15}$ are each substituted or unsubstituted $C_1$–$C_{18}$ alkyl or aryl wherein the substituted group is selected from a group consisting of aryl, halogen, hydroxy, amino, nitro, $C_1$–$C_5$ alkyl, $C_1$–$C_5$ alkoxy, and $C_2$–$C_5$ alkoxycarbonyl; and $R^{16}$ is hydrogen.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^{14}$ and $R^{15}$ are each substituted or unsubstituted aromatic hydrocarbon wherein the substituted group is selected from the group consisting of chloride, bromide, iodide, fluoride, —NO$_2$, —NMe$_2$, methoxy, and methyl; and $R^{16}$ is hydrogen.

In the most preferred embodiments: L and $L^1$ ligands are each either —P(cyclohexyl)$_3$ or —P(cyclopentyl)$_3$; X and $X^1$ ligands are each chloride; $R^{14}$ and $R^{15}$ are each substituted or unsubstituted phenyl or wherein the substituted group is selected from the group consisting of chloride, bromide, iodide, fluoride, —NO$_2$, —NMe$_2$, methoxy, and methyl; and $R^{16}$ is hydrogen.

When L and $L^1$ groups are triaryl phosphines, Reaction Scheme 3 may be modified by replacing a dihydrogen species in the starting complex with a third phosphine ligand. The resulting hydrido complex will be of the form $M(H)(Cl)(H_2)LL^1L^2$ or $M(H)(Cl)LL^1L^2$ depending on the starting dihydrogen species. In all other respects, M, X, $X^1$, $R^{14}$, $R^{15}$, and $R^{16}$ are as described above. Reaction Scheme 3A shows one version of this embodiment.

REACTION SCHEME 3A

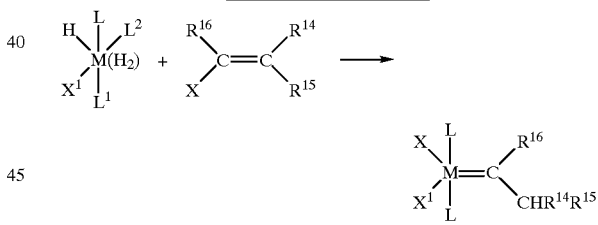

Because the alkene route reactions appears to be less efficient than the other two methods, the alkane route is generally the preferred method when non-vinyl alkylidene catalyst are to be synthesized. For example, Ru(H)(Cl)(H$_2$)(PCy$_3$)$_2$ reacts with vinyl chloride to give the expected carbene Ru(Cl)$_2$(PCy$_3$)$_2$(=CHCH$_3$), the methylidene complex Ru(Cl)$_2$(PCy$_3$)$_2$(=CH$_2$), and the ruthenium (IV) byproduct Ru(H)$_2$(Cl)$_2$(PCy$_3$)$_2$. The methylidene complex is a result of a subsequent cross metathesis reaction between the intended carbene product and vinyl chloride (which also results in the formation of 1-chloropropene). However, even when the total carbene products are taken into account, the ratio of carbene to Ru(IV) byproduct is a modest 2.1:1. Unlike the alkyne route, increasing the steric bulk at the alkene's β-carbon (to suppress β-addition), did not improve the carbene yield.

Alternative Synthesis for Ru(X)$_2$(L)$_2$(=CHR$^1$):

In this method, Ru(1,5-cyclooctadiene)(cyclooctatriene) (hereinafter referred to as "Ru(COD)(COT)") is used instead of the dihydrogen complex to synthesize catalysts of the general formula $Ru(X)_2(L)_2(=CHR^1)$ wherein:

R' is as previously defined in the catalyst section;

X is a halogen; and,

L is a phosphine of the formula $PR^3R^4R^5$, where $R^3$ is a secondary alkyl or cycloalkyl group, and $R^4$ and $R^5$ are independently selected from aryl, $C_1$–$C_{10}$ primary alkyl, secondary alkyl, or cycloalkyl groups. In preferred embodiments, X is chloride and L is $P(cyclohexyl)_3$, $P(cyclopentyl)_3$, or $P(isopropyl)_3$. $R^1CHX_2$ is added to a solution of Ru(COD)(COT) in the presence of phosphine, L, in a suitable solvent at room temperature to generate the product, $Ru(X)_2(L)_2$ $(=CHR^1)$. Illustrative examples of suitable solvents include but are not limited to toluene, benzene and dichloromethane.

The general mechanism of reaction involves two steps: the oxidative addition of the alkyl dihalide to the Ru(0) species followed by an α-halide elimination. An illustrative example of this method is shown in Reaction Scheme 4 which results in a 50% product yield of $RuCl_2(PCy_3)_2$ $(=CHPh)$.

REACTION SCHEME 4

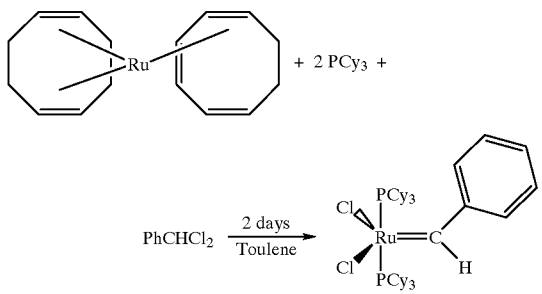

However, this synthetic route presents two potential limitations. The first is that although good yields have been reported, Ru(COD)(COT) is difficult and tedious to synthesize. The second is that the formation of phosphonium salts, such as $PCy_3CHClR^{1+}Cl^-$ when X=Cl and $L=PCy_3$, may potentially limit the viability of this route for some carbene catalysts. For example, while $RuCl_2(PCy_3)_2(=CHPh)$ and $RuCl_2(PCy_3)_2$ $(=CH_2)$ may be synthesized in this manner, $RuCl_2(PCy_3)_2(=CHCO_2Me)$ cannot be synthesized using $Cl_2CHCO_2Me$ because of the formation of the phosphonium salt, $[Cy_3PCHClCHCO_2Me]^+Cl^-$ as a side reaction.

Alternative Synthesis for RuCl2(PCy3)2(=CHPh):

This alternative route is a variation of the alkane route that was previously described and takes advantage of a potential metathesis reaction between the olefin used in the reaction and the carbene product. First, $RuCl_2(PCy_3)_2(=CHCO_2Me)$ is formed by reaction $Ru(H)_2(H_2)_2(PCy_3)$ with $Cl_2CHCO_2Me$ in the presence of the olefin, styrene, in an application of the above described alkane reaction. The formed carbene $RuCl_2(PCy_3)_2(PCy_3)(=CHCO_2Me)$ undergoes a subsequent metathesis reaction with styrene to produce the final product $RuCl_2(PCy_3)_2(=CHPh)$.

Experimental Procedures

Synthesis of $Ru(H)_2 (H_2)_2 (PCy_3)_2$.

In general, unless explicitly noted otherwise, all solvents used are degassed prior to use. $[RuCl_2(COD)]_x$ (6.0 g, 21.43 mmol), $PCy_3$ (12.0 g, 42.86 mmol), and NaOH (7.2 g) were placed in a 500 mL Fisher-Porter bottle. $[RuCl_2(COD)]_x$ is a polymeric complex produced from the reaction of $RuCl_3$ with COD. Degassed sec-butyl alcohol (250 mL) was added, and the suspension was pressurized under $H_2$ (2 atm) and heated at 90° C. The system was repressurized several times, an indication of $H_2$ uptake. The reaction mixture was stirred overnight. The system was allowed to cool to room temperature under $H_2$ pressure. A pale yellow crystalline precipitate was obtained. All of the following manipulations were carried out under $H_2$ pressure. Water (30 mL) was added to the resulting mixture, and the mixture was filtered though a glass frit filter. The filtrate was washed twice with water (30 mL portions) and with methanol (twice with 20 mL portions). The solid was dried under a $H_2$ stream. 11.8 g (83% yield) of a pale yellow crystalline compound was obtained. The NMR spectra of this product were identical to those previously reported in the literature for $Ru(H)_2(H_2)_2$ $(PCy_3)_2$.

Synthesis of $RuCl_2(PCy_3)_2(=CHPh)$.

To a suspension of $Ru(H)_2(H_2)_2(PCy_3)_2$ (1.0 g, 1.50 mmol) in pentane (40 mL), cyclohexene (1.5 mL, 14.80 mmol) was added. After 2 minutes, a yellow solution is obtained, and after 15 minutes, a pale yellow precipitate is formed. The reaction mixture was stirred for 1 hour. The volatiles were removed under vacuum. Pentane was added to the solid. Addition of $PhCHCl_2$ (0.4 mL, 3.11 mmol) led to the formation of a red solution, which was stirred for 45 minutes. The solvent was evaporated, and the residue was washed with cold methanol (three times with 10 mL portions). 0.75 g (61% yield) of a purple solid was obtained whose NMR spectra were identical to the compound $RuCl_2$ $(PCy_3)_2(=CHPh)$.

Synthesis of $RuCl_2(PCy_3)_2(=CH_2)$ and $RuCl_2(PCy_3)_2$ $(=CHCO_2Me)$.

$RuCl_2(PCy_3)_2(=CH_2)$ and $RuCl_2(PCy_3)_2(=CHCO_2Me)$ were prepared in an analogous manner as above except that $Cl_2CH_2$ and $Cl_2CHCO_2Me$ were added as the dihalo compounds respectively. In the case of the synthesis of $RuCl_2$ $(PCy_3)_2(=CH_2)$, because the reaction is slower as monitored by NMR, the reaction mixture was stirred overnight after the addition of $Cl_2CH_2$.

Selective spectroscopic data for $RuCl_2(PCy_3)_2$ $(=CHCO_2Me)$: $^1H$ NMR (300 MHz, $C_6D_6$: δ 20.15 (s, Ru=CH), 3.53 (s, CO2CH3); $^{13}C$ NMR (125.71, $CD_2Cl_2$, –30° C.) δ 276.37 (t, J(P,C)=5.1 Hz, Ru=CH), 178.69 (s, $CO_2Me$), 50.84 (S, $CO_2CH_3$); $^{31}P$ (161.9 MHz, $C_6D_6$) δ 38.66 (s, $PCy_3$); IR (Nujol) ν 1721 cm$^{-1}$ (C=O-(ester)).

$Ru(H)_2(H_2)_2(PCy_3)_2$+styrene +α,α-dichlorotoluene.

Styrene (0.2 mL, 1.7 mmol) was added to a solution of $Ru(H)_2(H_2)_2(PCy_3)_2$ (0.54 g; 0.77 mmol) in toluene (20 mL). After 15 min, α-dichlorotoluene (0.1 mL) was added to the resulting deep red solution. The reaction mixture was stirred for 45 min. The solvent was removed and the residue washed with methanol and acetone affording the isolation of a purple solid, identified as $Ru(=CHPh)Cl_2(PCy_3)_2$ by NMR. Yield 25%.

Isolation and utility of an alkane-reaction intermediate where the olefin is cyclohexene: $Ru(cyclohexene)_2(H_2)$ $(PCy_3)_2$.

Cyclohexene (5 mL was added to $Ru(H_2)(H_2)_2(PCy_3)_2^{13}$ (1.1 g; 1.65 mmol). The formation of a red solution was observed and immediately a pale yellow solid precipitated out. Pentane was added (20 mL) and the suspension was stirred for 2 h. The solid was isolated by filtration. Yield: 81%. $_1H$ in $C_6D_6$: −5. (br s, 2H, $H_2$), 1.2–2.0 (m, 66H, $PCy_3$), 3.0 (s, 1H, $CH_{olefin}$), 20.1 ppm; $^{31}P\{^1H\}$ 59 ppm (s).

Addition of $R^1CHX^1X$ to this intermediate, $Ru(cyclohexene)_2(H_2)(PCy_3)_2$ results in the ruthenium catalyst, $RuX^1X(PCy_3)_2(R^1)$. As a result, the specific intermediate, $Ru(cyclohexene)_2(H_2)(PCy_3)_2$, or any intermediate of the general form, $Ru(olefin)_2(H_2)(PCy_3)_2$, may replace $Ru(H)_2(H_2)_2(PCy_3)_2$ and the olefin in the alkane reaction route.

For example, $Ru(=CHPh)Cl_2(PCy_3)_2$ was synthesized by adding α,α-dichlorotoluene (5 μL) to a solution of $Ru(cyclohexene)_2 (H_2)(Cy_3P)_2$ (20 mg; 2.68•10-2 mmol) in $C_6D_6$ (0.5 mL) The solution turned deep red and the $^1H$ and $^{31}P\{^1H\}$ NMR spectra showed the quantitative conversion to $Ru(=CHPh)Cl_2(PCy_3)_2$. Similarly, $Ru(=CHCOOMe)Cl_2(PCy_3)_2$ was synthesized by adding methyl dichloroacetate (5 μL) to a solution of $Ru(cyclohexene)_2(H_2)(PCy_3)_2$ (20 mg; 2.68•10-2 mmol) in $C_6D_6$ (0.5 mL). The solution turned violet and the $^1H$ and $^{31}P$ NMR spectra showed the quantitative conversion to $Ru(=CHCOOMe)Cl_2 (PCy_3)_2$. $^1H$ in $C_6D_6$: 1.2–2.7 (m, 66H, $PCY_3$), 3.5 (s, 3H, $COOCH_3$), 20.1 ppm (s, CH carbene unit); $^{31}P\{^1H\}$ in $C_6D_6$ 38 ppm (s, $PCy_3$).

Synthesis of $Ru(H)(Cl)(H_2)_2(PCy_3)_2$.

$[RuCl_2(COD)]_x$ (4.00 g, 14.28 mmol) and tricyclohexylphosphine (8.46 g of 97% from Strem, 29.26 mmol) were placed in a 500 ml, high pressure system equipped with a pressure gauge. To this system, 200 mL of degassed sec-butanol and triethylamine (1.99 mL, 14.28 mmol) were added. The system is then placed under vacuum, and purged with hydrogen. After purging, the system is pressurized with 1.5 atm of hydrogen, sealed, and heated to 80° C. for a total of 20 hours. When the pressure dropped below an atmosphere the system was cooled and re-pressurized, approximately every 20–30 minutes for the first several hours.

Generation of $Ru(H)(Cl)(H_2)_2(PCy_3)_2$ can also be accomplished in a suitably sized, thick walled teflon-valved Strauss flask. Depending on the scale of the reaction and the size of the flask, the system is re-pressurized with hydrogen gas after several hours. Alternatively, the reaction can be carried out by bubbling $H_2$ gas at atmospheric pressure.

Isolation of the air-sensitive orange solid was accomplished by allowing the system to cool to room temperature and adding a volume (200 mL) of degassed methanol to insure complete precipitation. The solid was filtered, washed with methanol (3x, 50 mL, and dried in vacuo to give 9.26 g, 93% of $Ru(H)(Cl)(H_2)_2(PCy_3)_2$.

Synthesis of $RuCl_2(PCy_3)_2(=CH-CH=CMe_2)$.

Method A—alkyne route:

Ru(H)(Cl)(H2)(PCy3)2 (1.00 g, 1.43 mmol) under an inert atmosphere is dissolved in 30 mL of dichloromethane cooled to −30° C., and 3-chloro-3-methyl-1-butyne (170 μL, 1.5 mmol) is added. The solution instantly turns dark red-purple, and is allowed to stir for fifteen minutes before removing the flask from the cooling bath and concentrating to a viscous oil. Degassed methanol (20 mL) is added to precipitate the purple solid, which is then washed with methanol (3X, 10 mL) and dried to give 1.09 g or approximately 95.2% yield of the carbene.

Selected NMR data $(CD_2Cl_2)$: $^1H$:δ 19.26 (d, RuCH, $J_{HH}$=11.7 Hz), 7.81 (d, RuCHCH, $J_{HH}$=11.7 Hz); $^{31}P$:δ 36.4 (s, $RuPCy_3$); $^{13}C$: δ 288.4 (t, $Ru^CH$, $J_{CP}$=9.6 Hz) 146.9 (s), 133.5 (s).

NMR studies show that this reaction at −30° C. is extremely clean (no other carbene species) and proceeds to approximately 99%. At room temperature the reaction is less clean (i.e., other presumed and unidentified carbene species are generated in small quantities) but also proceeds in ~98% yield. Therefore, the use of low temperatures for the generation of this compound should give a slightly easier isolation and higher yield of a pure product. However, the generation of this carbene for use in situ can be done at room temperature with little or no visible effect.

All other reactions with $Ru(H)(Cl)(H_2)(PCy_3)_2$ described in the description portion of the specification were done in a similar fashion but on a 20 mg scale in 0.5 mL of $CD_2Cl_2$. Non commercially available alkynes were made following procedures in *Preparative Acetylenic Chemistry*, L. Brandsma, Elsevier Science Publishers B.V. (Amsterdam, 1988); H. Werner, et al., *Chem. Ber.* 122: 2097–2107 (1989); and K. Hiraki, et al., *J. Chem. Soci.,* Dalton Trans. pp. 873–877 (1985), all of which are incorporated herein by reference.

Method B—triarylphosphine version of the alkyne route 0.24 mL of 3-chloro-3-methyl-1-butyne was added to a −30° C. solution of $Ru(H)(Cl)(PPh_3)_3$ (2.0 g, 1.99 mmoles) in methylene chloride (20 ml). The reaction mixture was stirred for 1.5 hour at 0° C. After the volume was reduced to 1 mL under reduced pressure, 20 mL of pentane was added. The resulting brown solid was isolated by filtration, redissolved in 1 mL of methylene chloride and then was washed twice with 10 mL portions of pentane to yield 1.5 grams (90% yield) of the desired product.

Method C—in situ generation of $Ru(H)(Cl)(H_2)(PCy_3)_2$ $[RuCl_2(COD)]_x$ (0.500 g, 1.78 mmol) and tricyclohexylphosphine (1.050 g, 3.75 mmol) were placed in a 250 mL thick walled teflon-valved Strauss flask. To this system, 20 mL of degassed sec-butanol is added. The system is then placed under vacuum, purged with hydrogen, sealed, and heated to 80° C. After four hours the system is cooled to room temperature, re-pressurized with hydrogen, and allowed to stir at 80° C. for a further sixteen hours. The system is then cooled to room temperature and one volume of toluene is added. The resulting solution is cooled to −30° C. and 2-methyl-1-buten-3-yne (254 mL, 2.66 mmol) is added. After stirring for one hour the solution is concentrated by half and 50 mL of degassed methanol is added to give a purple solid, isolated as above to give 0.590 g, 41% of $RuCl_2 (PCy_3)_2(=CH-CH=CMe_2)$.

Synthesis of $RuCl_2(PCy_3)_2(=CH-CH=CMe_2)$—one pot method.

$[RuCl_2(COD)]_x$ (0.500 g, 1.79 mmol) and tricyclohexylphosphine (1.000 g, 3.58 mmol) were placed in a 500 mL high pressure system equipped with a pressure gauge. To this system, 25 mL of degassed sec-butanol and triethylamine (0.250 mL, 1.79 mmol) were added. After purging with hydrogen, the system was pressurized with 1.5 atm of hydrogen and heated to 80° C. for a total of 20 hours, repressurizing as needed. An orange precipitate, known to be $Ru(H)(H_2)_2Cl(PCy_3)_2$ is observed as well as a slightly brown solution. The apparatus was then cooled to room temperature, and then to 0° C., at which point it was purged with argon. 3-chloro-3-methyl-1-butyne (0.600 mL, 5.3 mmol) is added. Over a period of one hour the orange precipitate turns red-purple, and the reaction is then removed from the ice bath and allowed to stir for one additional hour. Degassed methanol (25 mL) is added to precipitate the purple solid, which is then washed with methanol (3×10 mL) and dried to give 1.35 g, 94.5% of the carbene. Selected NMR data $(CD_2Cl_2)$: $^1H$:d19.26 (d, RuCH, $J_{HH}$=11.7Hz, 1H), 7.81 (d, RUCHCH, $J_{HH}$=11.7Hz, 1H); $^{31}P$:d 36.4 (s, RuPCy3); $^{13}C$: d 288.4 (t, RuCH, $J_{CP}$=9.6HZ), 146.9 (s), 133.5 (s).

Synthesis of $RuCl_2(P^iPr_3)_2Cl_2Ru(=CH-CH=CMe_2)$—one pot method.

This procedure is identical to the one pot method for the synthesis of $RuCl_2(PCy_3)_2 (=CH-CH=CMe_2)$ except that triisopropyl phosphine (0.573 g, 3.58 mmol) is used instead of tricyclohexylphosphine. In this case the intermediate $Ru(H)(H_2)_2Cl (PiPr_3)_2$ is soluble, giving a red-brown solution which is then cooled and to which the 3-chloro-3-methyl-1-butyne is added. The reaction is quite vigorous, with gas evolved immediately and a deep purple precipitate observed. After stirring for thirty minutes the solid is isolated as above to give 1.85 g, 92.5% of the carbene. Selected NMR data (CD$_2$Cl$_2$):$^1$H:d19.38 (d, RuCH, J$_{HH}$=11Hz, 1H), 7.95 (d, RuCHCH, J$_{HH}$=11Hz, 1H), 2.80 (m, PCH(CH$_3$)$_2$, 6H), 1.54 and 1.26 (s, RuCHCHC(CH$_3$)$_2$, 3H each), 1.23 (dd, P PCH(CH$_3$)$_2$, 36H); $^{31}$P:d 45.8 (s, RuPCy3).

Synthesis of Poly-dicyclopentadiene using in situ generated catalyst.

The in situ generation of Ru$_2$Cl$_2$(PCy$_3$)$_2$(=CH—CH=CMe$_2$) (hereinafter referred to as the ruthenium carbene catalyst in this example) is accomplished by dissolving 18 mg (0.025 mmol) of Ru(H)(Cl)(H$_2$)$_2$(PCy$_3$)$_2$ in approximately 0.5–1.0 mL of dichloromethane under argon. This solution is cooled to −30° C., at which point 3-chloro-3-methyl-1-butyne (3.5 mL, 0.030 mmol) is added. The solution instantly turns red-purple, and is allowed to stir for fifteen minutes before removing the solvent to give a dark oil. If a solid is desired, the solution can be concentrated and a small amount (<1 mL) of degassed methanol can be added to give a purple solid, which is dried in vacuo (without filtration).

Polymerizations are done by placing the solution obtained below in a 40° C. oil bath for one hour, and then at least one hour in an oven at 100° C.

Method A:

The in situ generated ruthenium carbene catalyst is dissolved in 25 mL of DCPD and poured into a beaker.

Method B:

The in situ generated ruthenium carbene catalyst is dissolved in 5 mL of DCPD which contains 40 mg of triphenylphosphine, and allowed to stir under argon. After four hours the solution has become quite viscous and is added to 20 mL of DCPD in a beaker.

Method C:

The in situ generated ruthenium carbene catalyst is dissolved in 1 mL of DCPD which contains 40 mg of triphenylphosphine, and allowed to stir under argon. After 17 hours this solution has a slimy, soft gelatin like consistency, which can be dissolved in 4 mL of DCPD before being added to 20 mL DCPD in a beaker.

Ru(COD)(COT)+2 PCy$_3$+α,α—dichlorotoluene.

To a solution of Ru(COD)(COT)(0.11 g; 0.33 mmol) and PCy$_3$ (0.19 g; 0.67 mmol) in 15 mL of toluene was added α,α-dichlorotoluene (50 mL; 0.39 mmol). The reaction mixture was stirred at room temperature for two days. The resulting deep brown solution was evaporated, and the residue was washed with acetone and methanol (twice with 5 mL portions) affording the isolation of a purple solid. The NMR spectra of this product were identical to the compound Ru(=CHPh)Cl$_2$(PCy$_3$)$_2$. Yield: 50%.

Ru(H)$_2$(H$_2$)(PCy$_3$)$_2$+styrene+Cl$_2$CHCO$_2$Me.

Styrene (5 mL) was added to a suspension of Ru(H)$_2$(H$_2$)$_2$(PCy$_3$)$_2$ (3.0 g, 4.50 mmol) in pentane (50 mL). The red solution immediately obtained was stirred for 1 hour, and Cl$_2$CHCO$_2$Me (0.9 mL, 8.7 mmol) was then added. The reaction mixture was stirred for 45 minutes. The solvent was removed, and the residue was washed with acetone and methanol (twice with 20 mL portions). A purple solid (2.0 g, 54% yield) was isolated whose NMR data were identical to those of RuCl$_2$(PCy$_3$)$_2$(=CHPH).

What is claimed is:

1. A method of making a compound of the formula

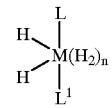

comprising:
  reacting [MXX$^1$(COD)]m with L and L$^1$ in the presence of NaOH and H$_2$ pressure of about 1.5 atm
wherein:
  m is an integer;
  n is 1 or 2;
  M is osmium or ruthenium;
  X and X$^1$ are independently selected from any anionic ligand;
  L and L$^1$ are independently selected from any neutral electron donor; and
  COD is cyclooctadiene.

2. The method as in 1 wherein the reaction takes place in a solvent.

3. The method as in claim 1 wherein M is ruthenium.

4. The method as in claim 1 wherein X and X$^1$ are the same and are both a halide.

5. The method as claim 1 wherein L and L$^1$ are the same and are both a triarylphosphine.

6. The method as in claim 5 wherein L and L$^1$ are both P(phenyl)$_3$.

7. The method as in claim 1 wherein L and L$^1$ are the same and are both a phosphine of the formula PR$^3$R$^4$R$^5$ wherein R$^3$ is a secondary alkyl or cycloalkyl group and
  R$^4$ and R$^5$ are independently selected from a group consisting of aryl, C$_1$–C$_{10}$ primary alkyl, secondary alkyl and cycloalkyl groups.

8. The method as in claim 7 wherein L and L$^1$ are selected from a group consisting of P(cyclohexyl)$_3$, P(cyclopentyl)$_3$, and P(isopropyl)$_3$.

9. The method as in claim 3 wherein the solvent is sec-butyl alcohol, X and X$^1$ are both chloride, and L and L$^1$ are the same and are selected from a group consisting P(cyclohexyl)$_3$, P(cyclopentyl)$_3$, and P(isopropyl)$_3$.

10. A method of making a compound of the formula Ru(H)$_2$(H$_2$)$_n$(L)$_2$ where, n is 1 or 2 and L is a phosphine of the formula PR$^3$R$^4$R$^5$ wherein R$^3$ is a secondary alkyl or cycloalkyl group and R$^4$ and R$^5$ are independently selected from a group consisting of aryl, C$_1$–C$_{10}$ primary alkyl, secondary alkyl and cycloalkyl groups, comprising:
  reacting [RuX$_2$(COD)]$_m$ with L in the presence of NaOH, secondary alcohol and H$_2$ wherein X is a halide and COD is cyclooctadiene.

11. A method of making a compound of the formula Ru(H)$_2$(H$_2$)$_n$(L)$_2$ where, n is 1 or 2 and L is a phosphine of the formula PR$^3$R$^4$R$^5$ wherein R$^3$ is a secondary alkyl or cycloalkyl group and R$^4$ and R$^5$ are independently selected from a group consisting of aryl, C$_1$–C$_{10}$ primary alkyl, secondary alkyl and cycloalkyl groups, comprising:
  forming a polymeric complex by contacting RuX$_3$ with cyclooctadiene and reacting the polymeric complex with L in the presence of NaOH and H$_2$ wherein X is a halide.

12. The method as in claim 2 wherein the reacting step occurs in a sec-butanol and X is chloride.

13. The method as in claim 2 wherein L is selected from a group consisting of P(cyclohexyl)$_3$, P(cyclopentyl)$_3$, and P(isopropyl)$_3$.

14. A method for making a compound of the formula

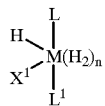

wherein, n is 1 or 2; M is osmium or ruthenium; $X^1$ is an anionic ligand; and L and $L^1$ are independently selected from any neutral electron donor, comprising:
reacting $[M(X^1)_2(COD)]_m$ with L and $L^1$ in the presence of $H_2$ wherein COD is cyclooctadiene and m is an integer.

15. The method as claim 14 wherein L and $L^1$ are the same and are both a triarylphosphine.

16. The method as in claim 14 wherein the reaction takes place in a solvent.

17. The method as in claim 14 wherein M is ruthenium, the solvent is sec-butanol and X is a halogen.

18. The method as in claim 17 wherein the sec-butanol contains triethylamine.

19. The method as in claim 14 wherein L and $L^1$ are the same and are both a phosphine of the formula $PR^3R^4R^5$ wherein
$R^3$ is a secondary alkyl or cycloalkyl group and
$R^4$ and $R^5$ are independently selected from a group consisting of aryl, $C_1$–$C_{10}$ primary alkyl, secondary alkyl and cycloalkyl groups.

20. The method as in claim 18 wherein L and $L^1$ are selected from a group consisting P(cyclohexyl)$_3$, P(cyclopentyl)$_3$, and P(isopropyl)$_3$.

21. The method as in claim 10 wherein the secondary alcohol is sec-butanol.

22. The method as in claim 10 wherein the $H_2$ pressure is about 1.5 atm.

23. A method of making a compound of the formula Ru(H)(X)(H$_2$)n(L)$_2$ where, n is 1 or 2, X is a halogen, and L is a phosphine of the formula $PR^3R^4R^5$ wherein $R^3$ is a secondary alkyl or cycloalkyl group and $R^4$ and $R^5$ are independently selected from a group consisting of aryl, $C_1$–$C_{10}$ primary alkyl, secondary alkyl and cycloalkyl groups, comprising:
reacting $[RUX_2(COD)]_m$ with L in the presence of $H_2$ wherein COD is cyclooctadiene and m is an integer.

24. The method as in claim 23 wherein the reacting step occurs in a solvent.

25. The method as in claim 23 wherein X is chloride and the solvent is sec-butanol.

26. The method according to claim 25 wherein the sec-butanol contains triethylamine.

27. The method according to claim 23 wherein L is selected from a group consisting of P(cyclohexyl)$_3$, P(cyclopentyl)$_3$, and P(isopropyl)$_3$.

28. A method of making a compound of the formula Ru(H)(X)(H$_2$)$_n$(L)$_2$ where, n is 1 or 2, X is a halogen, and L is a phosphine of the formula $PR^3R^4R^5$ wherein
$R^3$ is a secondary alkyl or cycloalkyl group and
$R^4$ and $R^5$ are independently selected from a group consisting of aryl, $C_1$–$C_{10}$ primary alkyl, secondary alkyl and cycloalkyl groups, comprising:
forming a polymeric complex by contacting $RuX_3$ with cyclooctadiene and reacting the polymeric complex with L in the presence of $H_2$.

29. The method as in claim 28 wherein the reacting step occurs in a solvent.

30. The method as in claim 28 wherein X is chloride and the solvent is sec-butanol.

31. The method according to claim 29 wherein the sec-butanol contains triethylamine.

32. The method according to claim 28 wherein L is selected from a group consisting of P(cyclohexyl)$_3$, P(cyclopentyl)$_3$, and P(isopropyl)$_3$.

33. A method of making a compound of the formula

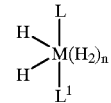

comprising:
reacting $[MXX^1(COD)]m$ with L and $L^1$ in the presence of NaOH and $H_2$ wherein:
m is an integer;
n is 1 or 2;
M is osmium;
X and $X^1$ are independently selected from any anionic ligand;
L and $L^1$ are independently selected from any neutral electron donor; and
COD is cyclooctadiene.

34. A method of making a compound of the formula

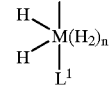

comprising:
reacting $[MXX^1(COD)]m$ with L and $L^1$ in the presence of NaOH and $H_2$ wherein:
m is an integer;
n is 1 or 2;
M is osmium or ruthenium;
X and $X^1$ are independently selected from any anionic ligand;
L and $L^1$ are independently selected from the group consisting of sulfonated phosphines, phosphites, phosphinites, phosphonites, arsines, stibines, ethers, amines, amides, imines, sulfoxides, carboxyls nitrosyls, pyridines, and thioethers; and
COD is cyclooctadiene.

* * * * *